United States Patent [19]
Subramanian

[11] Patent Number: 5,840,272
[45] Date of Patent: *Nov. 24, 1998

[54] IMAGING INFECTIOUS FOCI WITH HUMAN IGM 16.88

[75] Inventor: Ramaswamy Subramanian, Frederick, Md.

[73] Assignee: PerImmune Holdings, Inc., Rockville, Md.

[*] Notice: The term of this patent shall not extend beyond the expiration date of Pat. No. 5,548,882.

[21] Appl. No.: 701,420

[22] Filed: Aug. 22, 1996

Related U.S. Application Data

[63] Continuation-in-part of Ser. No. 346,988, Nov. 30, 1994, Pat. No. 5,549,882, which is a continuation of Ser. No. 899,661, Jun. 9, 1992, abandoned.

[51] Int. Cl.$^6$ .......................... A61K 51/00; A61K 36/14
[52] U.S. Cl. .................. 424/1.49; 530/388.8; 530/389.7
[58] Field of Search .................................. 424/1.49, 1.53; 530/388.8, 389.7

[56] References Cited

U.S. PATENT DOCUMENTS

| | | |
|---|---|---|
| 4,828,991 | 5/1989 | Hanna et al. . |
| 4,997,762 | 3/1991 | Hanna et al. . |
| 5,106,738 | 4/1992 | Hanna et al. . |
| 5,549,882 | 8/1996 | Subramanian ........................ 424/1.11 |

OTHER PUBLICATIONS

Subramanian et al., *Bioconjugate Chemistry*, 3:248–255 (1992), month not provided.

Tzen et al., *Journal of Nuclear Medicine*, 21:31–35 (1980), month not provided.

Fischman et al., *Journal of Nuclear Medicine*, 31:1119–1205 (1990), month not provided.

Rubin et al., *The New England Journal of Medicine*, 321:14:935–939 (1989), month not provided.

Vallabhajosula et al., *J. of Nuclear Medicine*, 33(Supp) Abs. 877, p. 1031, month not provided.

Steis et al., *Biological Abstracts*, 89(11), Abstract 117429 (Jun. 1990), month not provided.

Ryan et al., *Radiology*, 167(1):71–75 (1988), month not provided.

Goldenberg et al., *In vivo antibody imaging for detection of human tumors*, Goldenberg, Ed., pp. 273–292 (1990), month not provided.

Steis et al., *J. Clin. Oncol.*, 8(3):476–490, (1990), month not provided.

Sarafini et al., *J. Nucl. Med.*, 32:2227–2232, (1991), month not provided.

Datz et al., *J. Nuc. Med.*, 35:1:74–83, (1994), month not provided.

Buscombe et al., *J. Nuc. Med.*, 34:10:1621–1625, (1993), month not provided.

*Primary Examiner*—Gary E. Hollinden
*Assistant Examiner*—Dameron Jones
*Attorney, Agent, or Firm*—William M. Blackstone

[57] ABSTRACT

A method for imaging foci of infection by administering radiolabeled human IgM 16.88 and detecting sites of localization.

6 Claims, 2 Drawing Sheets

IMAGING INFECTIOUS FOCI WITH HUMAN IGM 16.88

This application is a continuation-in-part of U.S. patent application Ser. No. 08/346,988 filed Nov. 30, 1994 now U.S. Pat. No. 5,549,882; which is a continuation of U.S. patent application Ser. No. 07/899,661 filed Jun. 9, 1992, now abandoned.

This invention relates to imaging sites of infection using human IgM 16.88, a human monoclonal antibody raised especially for targeting antigens associated with colorectal carcinoma tumors. Surprisingly, this monoclonal antibody also localizes to sites of infection and can be used for imaging infectious foci resulting from any conditions and diseases that cause inflammation, including bacterial infections, viral infections, fungal infections and autoimmune diseases.

BACKGROUND OF THE INVENTION

Recently there has been an increase in the use of monoclonal antibodies for diagnostic and therapeutic applications in vivo. Successful attempts have been made to locate tumor lesions of size greater than 5 mm using radiolabeled monoclonal antibodies and gamma camera imaging. It was hypothesized that in most of these cases specific antigen binding at the tumor site was responsible for the localization of radiolabeled antibody.

The popular radiopharmaceuticals useful for infection imaging in humans include gallium-67 citrate, indium-111 and technetium-99m labeled leukocytes, and indium-111 labeled white blood cells. Gallium-67 based radiopharmaceuticals may not be useful for the evaluation of infections in the abdomen as physiological excretion by the bowel is a disadvantage for this reagent. Leukocyte and white blood cell labeling procedures are complicated and there is always a potential for cellular contamination. Recent clinical studies have demonstrated that indium-111 labeled and technetium-99m labeled polyclonal IgG antibodies localize at the site of bacterial and viral infections in a variety of cases (Datz et al., "The Efficacy of Indium-111-Polyclonal IgG for the Detection of Infection and Inflammations," *The Journal of Nuclear Medicine*, 1994: 35, No. 1, 74–83). Pooled human immunoglobulin labeled with indium-111 has been used to identify the presence and extent of infection in patients positive for human immunodeficiency virus (HIV) presenting with symptoms of acute infection (Buscombe et al., "Indium-111-Labeled Polyclonal Human Immunoglobulin: Identifying Focal Infection in Patients Positive for Human Immunodeficiency Virus," *The Journal of Nuclear Medicine*, 1993: 34, No. 10, 1621–1625). These studies demonstrate that they are the infectious foci or inflammation sites and not foreign material or organisms that are imaged. Bacterial infections, viral infections, fungal infections and sites of autoimmune inflammation and trauma are imaged.

In 1988 Rubin et al. discovered the use of radiolabeled, non-specific polyclonal human immunoglobulin for the detection of focal inflammation by scintigraphy (Rubin, R. H., Fischman, A. J., Callahan, R. J. et al., "In(111) Labeled Nonspecific Immunoglobulin Scanning in the Detection of Focal Infection", N. Eng. J. Med., 1989: 30:385–389). It was shown that In(111)-IgG was superior to other radiopharmaceuticals such as Ga(67)-citrate and In-111 labeled white blood cells. Several other investigators have also found that radiolabeled polyclonal IgG localizes well in infectious foci. The reason for localization of these radiopharmaceuticals in infection is not well understood. In the case of Ga(67)-citrate, the protein leakage of the radiometal may be responsible for the localization of Ga(67)-transferrin at the infectious sites (Tzen, K. Y., Oster, Z. H., Wagner, H. N., et al., "Role of Iron-Binding Proteins and Enhanced Vascular Permeability in the Accumulation of Gallium-67", Journal of Nuclear Medicine, 1980:21, 31–35.) Rubin et al. had considerable success using radiolabeled human polyclonal IgG antibodies in clinical trials. They further showed that Fab fragments of IgG did not localize to the infectious sites, whereas IgG and Fc fragments did. They also reported that the localization of In(111) labeled IgG substantially exceeded the localization of other compounds such as Tc(99) labeled human serum albumin and Ga(67)-citrate (Fischman, A. L., Rubin, R. H., White, J. A., et al. "Localization of Fc and Fab Fragment of Nonspecific Polyclonal IgG at Focal Sites of Inflammation," J. Nucl. Med., 1990:31, 1199–1205). The blood clearance half-times ($t_{1/2}$) in hours were:

IgG—36.4
Fc —32.5
½Fc—22.3
Fab—12.8

Because of the fast clearance times one would expect ½Fc and/or Fab to be superior to IgG or Fc for imaging infections. However, animal experiments clearly showed that ½Fc and Fab fragments are relatively poor infection imaging agents.

Although it is not clear why immunogobulins localize to sites of infection, polyclonal IgG were shown to localize to infectious foci of various causes. In addition to bacterial infections, possible viral infection (CMV) and trauma (fracture and hematoma) were also imaged, demonstrating that it is the inflammation, not the causative organism, to which antibodies generically localize (Serafini et al., "Clinical Evaluation of a Scintigraphic Method for Diagnosing Inflammations/Infections Using Indium-111-Labeled Nonspecific Human IgG," *J. Nucl. Med.* 1991: 32, 2227–2232).

In all of the above cases the image quality is often poor due to high uptake of radioactivity in normal tissues and the slow clearance of the macromolecule from circulation. To avoid some of these disadvantages, radiolabeled chemotactic peptides have been used to image infections in animals and humans. However, with these low molecular weight peptides, although the target to nontarget ratio is high, the absolute abscess uptake is relatively low, making it difficult to obtain good images.

SUMMARY OF THE INVENTION

This invention is a method for imaging foci of infection using radiolabeled human IgM 16.88.

BRIEF DESCRIPTION OF THE DRAWINGS

FIG. 1 illustrates imaging of inflammation in rabbits using In(111) labeled polyclonal IgG.

FIG. 2 illustrates imaging of inflammation in rabbits using In(111) labeled IgM 16.88.

DESCRIPTION OF PREFERRED EMBODIMENTS

Figure 1A:
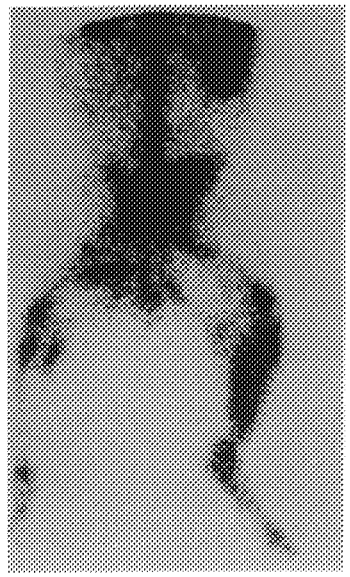
FIGS. 1a and 1b are images at 4 hours.

The present invention demonstrates the use human monoclonal antibody 16.88 of isotype IgM in imaging of infectious foci. Furthermore, this invention shows that In(111) labeled 16.88 is superior to In(111) labeled human polyclonal IgG and In(111) labeled human monoclonal IgG for imaging of infectious sites. Human monoclonal antibody 16.88 is produced by the cell line LiCo 16.88, deposited with the American Type Culture Collection, Rockville, Md., U.S.A., Accession Number HB 8495, claimed in U.S. Pat. No. 4,997,762, which is included herein in its entirety by reference.

Often external imaging of lesions and infections depends on the target to non-target ratio of the radiopharmaceutical under investigation. In general, the larger the ratio the better the quality of the image. In imaging infectious foci this is of particular importance due to the non-specificity associated with the localization of immunoglobulins. The biological half life of IgM antibodies is 5 days, which is relatively short when compared with the half life of IgG antibodies (23 days) (Immunology Immunopathology and Immunity, Stewart Sell, 4th Edition, Elsevier, New York, 1987, pp. 87).

We compared the behavior of polyclonal IgG and human IgM monoclonal antibody 16.88 radiolabeled with indium-111 using the bifunctional chelating agent LiLo, 1,3-bis[N-N(2-aminoethyl)-2-aminoethyl]-2-aminoacetamido]-2-(4-isothiocyanato-benzyl)propane-N,N,N',N'',N''',N''',N'''',N'''', N''''-octaacetic acid, with reference to their ability to localize at the site of infection in rats and rabbits. Analysis of the results indicated that the human IgM monoclonal antibody exhibited the best behavior for external imaging of the site of infection. 16.88 is rapidly picked up by the reticuloendothelial system and removed from circulation by the liver and spleen. This rapid clearance of 16.88 associated with specific uptake in infectious sites leads to high target to non-target ratios in animals bearing infectious organisms.

EXAMPLE I

Human monoclonal antibodies were produced by Epstein-Barr virus transformed human lymphoblastoid cell lines derived from peripheral blood lymphocytes of colon carcinoma patients immunized with autologous tumor vaccines by methods taught in U.S. Pat. No. 4,828,991 and U.S. Pat. No. 5,106,738, which are also included herein by reference.

Five different antibody preparations were analyzed with reference to their ability to localize in infectious foci. Note that LiLo refers to a novel bifunctional chelating agent suitable for attaching radiometals such as Indium111 to monoclonal antibodies (Subramanian, R., Colony, J., Shaban, S., Sidrak, H., Haspel, M. V., Pomato, N, Hanna, Jr., M. G. and McCabe, R. P., "New Chelating Agent for Attaching Indium111 to Monoclonal Antibodies: In Vitro and In Vivo Evaluation", Bioconjugate Chemistry, 1992: 3, 248–255 and copending application USSN 07/773,753 (now abandoned) by Subramanian et al., both of which are also included herein by reference.) CO126CV154, CO126CV64 and CO126MV163 were prepared by PerImmune, Inc., Rockville, Md.
1. IgM—16.88-LiLo
2. IgG—CO126CV154-LiLo
3. IgG—CO126CV64-LiLo
4. IgG—CO126MV163-LiLo
5. IgG polyclonal-LiLo Preparation of In(111)-antibodies:

0.1 ml of antibody-LiLo complex (0.6–0.8 mg) was labeled with 0.4 mCi of In(111) using acetate and citrate buffers. A small amount of DTPA was added at the end of the reaction to scavenge unbound In(111), and the reaction mixture was purified by G50-70 gel filtration chromatography. The percentage of In(111) bound to the antibody was determined using ascending thin layer chromatography (solvent system: 50/50 mixture of methanol and 0.1M ammonium acetate buffer solution). For all preparations the labeling efficiency (LE) was greater than 95% (Table 1).

Another method for labeling the conjugate is as follows:

Antibody-LiLo conjugate (0.1–100 mg) in phosphate buffered saline solution (pH 7.2) is added to indium-111 chloride (0.1–10 mCi) in a mixture (1:1 v/v) of acetate solution, 0.6M, pH 5.5, and citrate solution, 0.06M, pH 5.5. The reaction mixture is incubated at room temperature for 30–45 minutes and an aliquot of DTPA solution is added to scavenge the excess unbound indium-111. The reaction mixture is further purified by gel filtration column chromatography, if necessary.

The percentage of indium111 bound to the antibody is determined using ascending thin layer chromatography (solvent system: 50/50 mixture on 0.1M acetate solution and methanol) or ITLC-SG strips (solvent system: phosphate buffered solution, 0.05M, pH 7.2). In general, the radiolabeling efficiency (percentage of indium-111 bound to MoAb) is greater than 95% under the experimental conditions.

Animal Model:

Male rats (100–120 g) were injected in the right thigh muscle with 0.1 ml of cell suspension containing $2 \times 10^6$ *E. coli* per ml. The left leg served as a control. The rats developed severe infection within 24 hours as indicated by swelling of the right thigh and inability to use the leg.

Results:

All images were read qualitatively on a scale of +, 1+, 2+, 3+ based on the intensity of radioactivity at the site of infection. The results are shown in Table 2. Analysis of the image data revealed that all antibody preparations localized at the infectious site. However, greater than 70% of the images with IgM were graded at the highest level and showed less soft tissue uptake compared with IgG images. No differences were observed between monoclonal IgG and polyclonal IgG images.

Figure 1B:
Figure 1C:
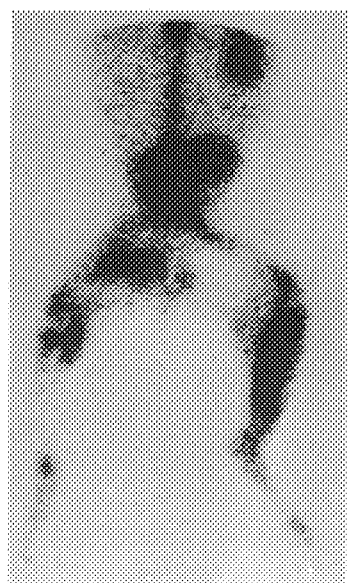
FIGS. 1c and 1d are images at 24 hours.
Figure 1D:
Figure 2A:
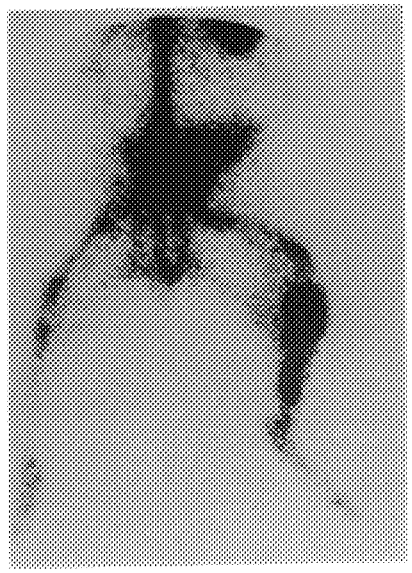
FIGS. 2a and 2b are images at 4 hours.
Figure 2B:
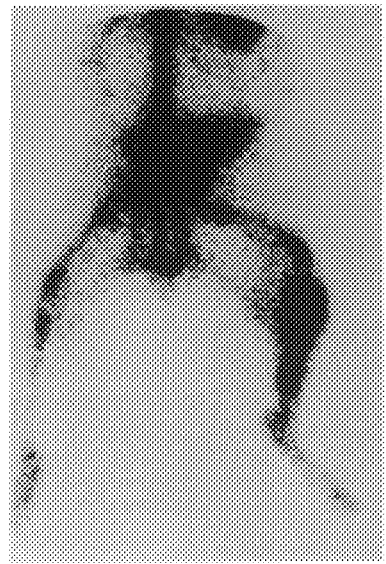
Figure 2C:
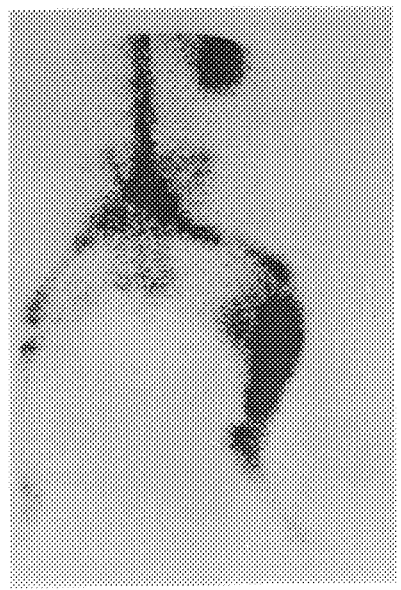
FIGS. 2c and 2d are images at 24 hours.
Figure 2D:
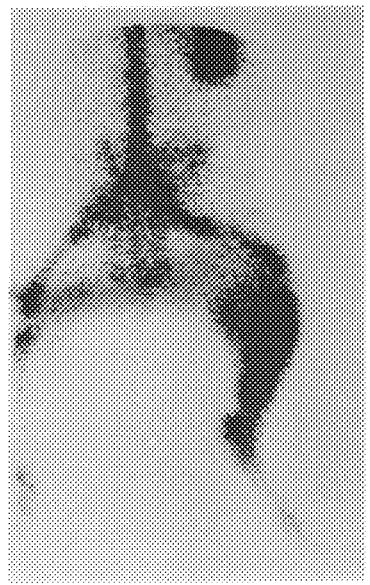

The above results were also confirmed using rabbit models. The images with In(111)-16.88 were the best at 4 hours with higher target/soft tissue ratios. The right leg in each rabbit can be seen to provide the denser image in the area inflammation compared with the left leg. The images of the polyclonal IgG in FIG. 1 and the monoclonal IgM in FIG. 2 demonstrated that the IgM provides significantly less non-specific background binding at both the 4 hour and 24 hour images. Also, the comparative image density between the right leg with the infectious foci and the left leg, which was free of inflammation, provided significantly greater comparative image density using 16.88. These results demonstrate that sites of infection can be imaged in vivo in subjects who are free of tumor tissue with which human IgM 16.88 reacts.

16.88-LiLo.In(111) has been shown to be safe for human administration, as 16.88-LiLo.In(111) has been used in the preoperative staging of breast cancer and in other clinical trials. It has been suggested that the identification by radioimmunoscintigraphy and the removal by inoperative sampling of lymph nodes detected by In(111)-LiLo.16.88 may be clinically useful and selectively limit the surgical staging procedure. In several clinical studies involving 16.88 labeled with I-131, In-111, Re-186, no detectable levels of human anti-human antibody (HAHA) was detected. Murine derived anti-granulocyte antibodies, although reported to localize well at infectious foci, have the potential to elicit immune responses leading to formation of human anti-murine monoclonal antibodies (HAMA). Thus, repeat infusions into the same patient becomes difficult. Also, with 16.88 we are not limited by the amount of antibody dose. As high as 1000 mg of 16.88 has been administered to patients without significant toxicity or immune response. Hence, 16.88 is safe and non-immunogenic. In addition, earlier dosimetry calculations based on mice biodistribution studies to estimate radiation dose to patients did not exceed 1.5 rad to any organ per mCi of In(111)-LiLo-16.88.

Any radioactive labels useful for imaging can be used for labeling human IgM 16.88. In the preferred embodiment, In(111) is the radioactive label. However, Tc(99m), Cu(67), Ga(67), I(123) and I(131) may also be used for imaging infectious foci. Such use of these radioactive labels is taught in the prior art discussed above.

The labeled IgM 16.88 is administered by conventional means. Normally intravenous administration is used, although intraperitoneal administration is preferred when the infection is exposed to the peritoneal cavity.

Conventional quantities of labeled IgM 16.88 are used for imaging. Preferably, approximately 5mCi/70 Kg of body weight is administered. Overall, effective imaging should be obtainable through administering about 1 to 10 mCi/70 Kg. The preferred range is 2 to 5mCi/70 Kg of body weight. When using short lived isotopes such as Tc-99m and I-123, 10–40 mCi of radioactivity will be required. Of course, as well known in the art, smaller overall quantities may be used when administering to known sites of infection. The labeled conjugates are prepared as described in Subramanian et al., Supra. Screening is conducted using a planar gamma scintillation camera. Methods for administration and scanning useful with the invention are the same as those taught by Steis, R. G. et al., "Toxicity, Immunogenicity, and Tumor Radioimmunodetecting Ability of Two Human Monoclonal Antibodies in Patients with Metastatic Colorectal Cancer," *J. Clin. Oncol.* 1990: 8(3), 476–490, for which purpose this article is to be included herein by reference.

Human Studies:

Human studies are performed as follows. Patients suspected of bacterial infections, viral infections (such as Cytomegalovirus), fungal infections or localized autoimmune disease inflammation are infused intravenously with 0.1 to 100 mg of 16.88-LiLo.In(111) containing 0.1 to 10 mCi of indium-111 in a volume of 0.25 to 100 ml of saline solution. Using a suitable gamma camera and computer, anterior and posterior planar images of the various regions of the patient, such as the abdomen, pelvis, chest, and arm and leg joints are obtained at 2–6 hours, 8–24 hours, and 26–72 hours post injection of the radiolabeled antibody dose. In some cases single photon emission computed tomography (SPECT) images are also obtained. These methodologies are well known in the art, see for example Buscombe et al, supra.

The images obtained from these patients treated with indium-111 labeled 16.88-LiLo are read by nuclear medicine specialists. Presence of diffuse or focal radioactive uptake compared to surrounding soft tissue indicates the presence of infectious foci. Standard microbiological and histopathological studies or other imaging modalities, such as computed tomography, ultrasound, and magnetic resonance imaging are performed to confirm the presence of infection.

The essence of this invention is the discovery that a human IgM antibody obtained from human B-cells taken from colorectal cancer patients immunized using autologous tumor vaccines, which is well known for its specificity to colorectal carcinoma associated antigens, can be used for imaging sites of infection from any origin in subjects who are essentially free of tumor tissue. Accordingly, radioactive labels, chelators and methods of administration known in the art that are used to facilitate the imaging of infectious foci with human IgM 16.88 are well within the scope of the invention as set forth in the claims that follow.

TABLE 1

IMAGING STUDIES IN RATS WITH INFECTION

| Tracer | L.E. (%) | # Rats | Imaging studies performed at | | | | |
|---|---|---|---|---|---|---|---|
| | | | 0.5 | 1 | 2 | 4 | 24 hrs. |
| IgM 16.88 | 97.9 | 5 | X | X | X | X | X |
| IgG-CV154 | 98.4 | 5 | X | X | X | X | X |
| IgM 16.88 | 96.4 | 8 | | | | X | X |
| IgG-CV154 | 96.8 | 7 | | | | X | X |
| IgG-MV163 | 95.5 | 7 | | | | X | X |
| IgG-CV64 | 51.3 | | not studied in animals | | | | |
| IgG-CV64 | 97.2 | 6 | | | | X | X |
| IgG-poly | 98.1 | 7 | | | | X | X |

TABLE 2

Results of In-Antibody Imaging Data

| Tracer | # Rats | Time of Imaging Study (hr) | Uptake** | | | | Fraction Positive (2+ or greater) |
|---|---|---|---|---|---|---|---|
| | | | + | 1+ | 2+ | 3+ | |
| In-LiLo | 3 | 0.25 | | | | | 0/3 |
| | | 0.5 | | | | | 0/3 |
| | | 1 | | | | | 0/3 |
| | | 2 | | | | | 0/3 |
| | | 4 | | | | | 0/3 |
| In-TF* | 4 | 2 | 1 | 1 | 2 | | 2/4 |
| | | 4 | | 1 | 2 | 1 | 3/4 |
| | | 24 | 1 | 1 | 1 | 1 | 2/4 |
| $^{67}$Ga-Citrate | 6 | 4 | | | 2 | 4 | 4/6 |
| In-IgM 16.88 | 5 | 4 & 24 | | | 3 | 1 | 4/5 |
| In-IgG | 5 | 4 & 24 | | | 3 | | 3/5 |
| In-IgM 16.88 | 7 | 4 | | | 2 | 5 | 5/7 |
| | | 24 | | 1 | 2 | 4 | 6/7 |
| In-IgG CV154 | 6 | 4 | | | 2 | 4 | 4/6 |
| | | 24 | | 1 | 3 | 2 | 5/6 |
| In-IgG MV163 | 7 | 4 | | | 4 | 2 | 2/7 |
| | | 24 | | 1 | 3 | 1 | 4/7 |
| In-IgG CV64 | 6 | 4 | | 1 | 3 | 2 | 5/6 |
| | | 24 | | 1 | 4 | 1 | 5/6 |
| In-IgG-poly | 7 | 4 | | 2 | 4 | 1 | 5/7 |
| | | 24 | | | 2 | 5 | 5/7 |

*Transferrin
**2+ Uptake Cutoff for Positive Image

TABLE 3

IMAGING STUDIES IN RABBITS WITH INFECTION: COMPARISON
OF 3 In(111) LABELED ANTIBODIES WITH In(111) TRANSFERRIN

| Tracer | L.E. (%) | # Rabbits | Imaging studies performed at | |
|---|---|---|---|---|
| | | | 4 hrs. | 24 hrs. |
| IgM-16.88 | 97.5 | 2 | X | X |
| IgG-CV64 | 98.0 | 2 | X | X |
| IgG-poly | 97.5 | 2 | X | X |
| In-TF (plasma) | | 2 | X | X |

I claim:

1. A method for imaging infectious foci in an animal comprising administering radiolabeled human IgM 16.88, ATCC accession number HB 8495, to the animal in an amount effective for detection by scanning, scanning said animal to detect the radiolabeled 16.88 and identifying the location of the radiolabeled 16.88, identifying the location of infectious foci thereby.

2. The method of claim 1, wherein the human IgM 16.88 is radiolabeled with a radionuclide selected from the group consisting of Tc(99m), Cu(67), Ga(67), I(123), I(131) and In(111).

3. The method of claim 2, wherein the radionuclide is In(111).

4. The method of claim 1, wherein the animal is a man and the infectious foci are sites of autoimmune disease inflammation.

5. The method of claim 1, wherein the animal is a man and the infectious foci are sites of viral infection.

6. The method of claim 1, wherein the animal is a man and the infectious foci are sites of fungal infection.

* * * * *